(12) United States Patent
Suzuki et al.

(10) Patent No.: US 8,945,123 B2
(45) Date of Patent: Feb. 3, 2015

(54) HIGH-FREQUENCY TREATMENT TOOL

(75) Inventors: Keita Suzuki, Tokyo (JP); Hideki Fujii, Tokyo (JP)

(73) Assignee: Olympus Medical Systems Corp., Tokyo (JP)

(*) Notice: Subject to any disclaimer, the term of this patent is extended or adjusted under 35 U.S.C. 154(b) by 259 days.

(21) Appl. No.: 13/223,780

(22) Filed: Sep. 1, 2011

(65) Prior Publication Data

US 2012/0059373 A1 Mar. 8, 2012

Related U.S. Application Data

(63) Continuation of application No. PCT/JP2010/070547, filed on Nov. 18, 2010.

(30) Foreign Application Priority Data

Jan. 18, 2010 (JP) ................................ P2010-008003

(51) Int. Cl.
*A61B 18/16* (2006.01)
*A61B 18/14* (2006.01)
*A61B 17/00* (2006.01)

(52) U.S. Cl.
CPC ..... *A61B 18/1492* (2013.01); *A61B 2017/0088* (2013.01); *A61B 2018/1407* (2013.01); *A61B 2018/141* (2013.01); *A61B 2018/1412* (2013.01); *A61B 2018/162* (2013.01)
USPC ............................................. 606/47; 606/113

(58) Field of Classification Search
CPC .................. A61B 18/1492; A61B 2018/1407; A61B 2018/141; A61B 2018/1465; A61B 2018/1475; A61B 2018/162
USPC ................... 606/41, 46, 47, 110, 113, 29, 39; 607/98, 99, 115
See application file for complete search history.

(56) References Cited

U.S. PATENT DOCUMENTS 4,311,143 A * 1/1982 Komiya ........................... 606/47
5,417,697 A * 5/1995 Wilk et al. ..................... 606/113

(Continued)

FOREIGN PATENT DOCUMENTS

DE  29 41 060 A1  4/1980
DE  196 30 601 A1  2/1997

(Continued)

OTHER PUBLICATIONS

International Search Report PCT/JP2010/070547 dated Dec. 21, 2010.

(Continued)

*Primary Examiner* — Michael Peffley
*Assistant Examiner* — Thomas Giuliani
(74) *Attorney, Agent, or Firm* — Scully, Scott, Murphy & Presser, PC (57) ABSTRACT

A high-frequency treatment tool (1) includes an operating wire (12) having a treatment part (10) including a treatment electrode; a first tube (23) formed from an insulating material, in which the operating wire (12) for enabling the treatment part (10) to protrude and recede is inserted; and a second tube (21) having a passive electrode (22) at a distal end, in which inserted the first tube (23) such as to cover an inner peripheral face of the passive electrode (22) is inserted. An engagement part (25) and an engaged part (22C) that can engage with each other are formed in the first tube (23) and the passive electrode (22), and the engagement of the engagement part (25) with the engaged part (22C) restricts the relative movement of a distal-end part of the first tube (23) to a proximal-end side of the first tube (23) with respect to the passive electrode (22).

5 Claims, 7 Drawing Sheets

(56) References Cited

U.S. PATENT DOCUMENTS

| | | | |
|---|---|---|---|
| 5,667,525 A | | 9/1997 | Ishibashi |
| 5,843,019 A | * | 12/1998 | Eggers et al. ............... 604/22 |
| 6,048,340 A | | 4/2000 | Miyagi |
| 2007/0198011 A1 | | 8/2007 | Sugita |

FOREIGN PATENT DOCUMENTS

| | | |
|---|---|---|
| DE | 10 2007 008 272 A1 | 8/2007 |
| JP | 55-52748 A | 4/1980 |
| JP | 9-38103 A | 2/1997 |
| JP | 2002-224135 A | 8/2002 |
| JP | 2006-280662 A | 10/2006 |

OTHER PUBLICATIONS

Supplementary European Search Report dated Jan. 12, 2012 from corresponding European Patent Application No. EP 10 84 3114.9.

* cited by examiner

FIG. 11

HIGH-FREQUENCY TREATMENT TOOL

The present application is a US Continuation Application based on PCT/JP2010/070547 filed in Japan on Nov. 18, 2010, which is based on Japanese Patent Application No. 2010-008003, filed Jan. 18, 2010, and claims priority on the aforementioned application, the content of which is incorporated herein by reference.

TECHNICAL FIELD

The present invention relates to a high-frequency treatment tool, and more particularly to a bipolar high-frequency treatment tool that includes a first electrode and a second electrode.

BACKGROUND ART

There is a conventionally known high-frequency treatment in which a high-frequency current is passed through a treatment part, and this electrical energy is used to perform various treatments to a living tissue, such as cutting it off. Among the most commonly known high-frequency treatment tools are a monopolar (single electrode) type, which includes a treatment electrode (first electrode) provided at the treatment part and a passive electrode (second electrode) disposed outside the body of the patient, and a bipolar type, which includes the passive electrode disposed at a distal end of the treatment part.

In a bipolar high-frequency treatment tool, due to the close proximity between the treatment electrode and the passive electrode, shorting caused by contact between them is more likely to occur than in the monopolar type. When a short occurs, treatment cannot be performed to the living tissue. Therefore, it is important, in a bipolar high-frequency treatment tool, to ensure that there is sufficient insulation between the treatment electrode and the passive electrode, particularly during the treatment.

One example of a structure for ensuring insulation between the treatment electrode and the passive electrode is, for example, the bipolar high-frequency treatment tool disclosed in Patent Document 1. In this high-frequency treatment tool, an insulating tube is inserted into an outer tube with a passive electrode attached to its distal end, and a driving wire with a treatment electrode provided at its distal end is inserted into the insulating tube. The insulating tube is adhesively fixed such as to cover the inner peripheral face of the passive electrode, and its presence between the treatment electrode and the passive electrode ensures that they are insulated from each other.

PRIOR ART DOCUMENT

Patent Document

Patent Document 1: Japanese Unexamined Patent Application, First publication No. 2002-224135

DISCLOSURE OF THE INVENTION

It is an object of the present invention to provide a high-frequency treatment tool that can be manufactured easily and efficiently, and can reliably prevent shorting between a treatment electrode and a passive electrode.

Means for Solving the Problems

The invention employs the following means. A high-frequency treatment tool according to the invention includes: an operating wire having a treatment part including a treatment electrode; a first tube formed from an insulating material, in which the operating wire for enabling the treatment part to protrude and recede is inserted; and a second tube having a passive electrode at a distal end, in which the first tube is inserted so as to cover an inner peripheral face of the passive electrode. An engagement part and an engaged part that can engage with each other being formed in the first tube and the passive electrode; and the engagement of the engagement part with the engaged part restricts the relative movement of a distal-end part of the first tube to a proximal-end side of the first tube with respect to the passive electrode.

In the high-frequency treatment tool described above, one of the engagement part and the engaged part can be formed by hot shaping at the distal-end part of the first tube.

In the high-frequency treatment tool described above, one of the engagement part and the engaged part can be formed by pressing-in a shape-preserving member at the distal-end part of the first tube.

The engagement part can be a large-diameter part provided to the first tube. Furthermore, the engagement part can be a large-diameter part that is provided to the first tube and engages with the engaged part on the proximal-end side of the distal end of the passive electrode. Moreover, the second tube can include a flexible tube main body and a blade made from metal wires that is provided in an inner cavity of the tube main body, the blade and the passive electrode can be electrically connected.

Effects of the Invention

The high-frequency treatment tool according to the invention can be manufactured easily and efficiently, and can prevent shorting between the treatment electrode and the passive electrode.

BEST MODES FOR CARRYING OUT THE INVENTION

A high-frequency treatment tool according to a first embodiment of the invention will be explained with reference to FIG. 1 to FIG. 4B.

Figure 1:
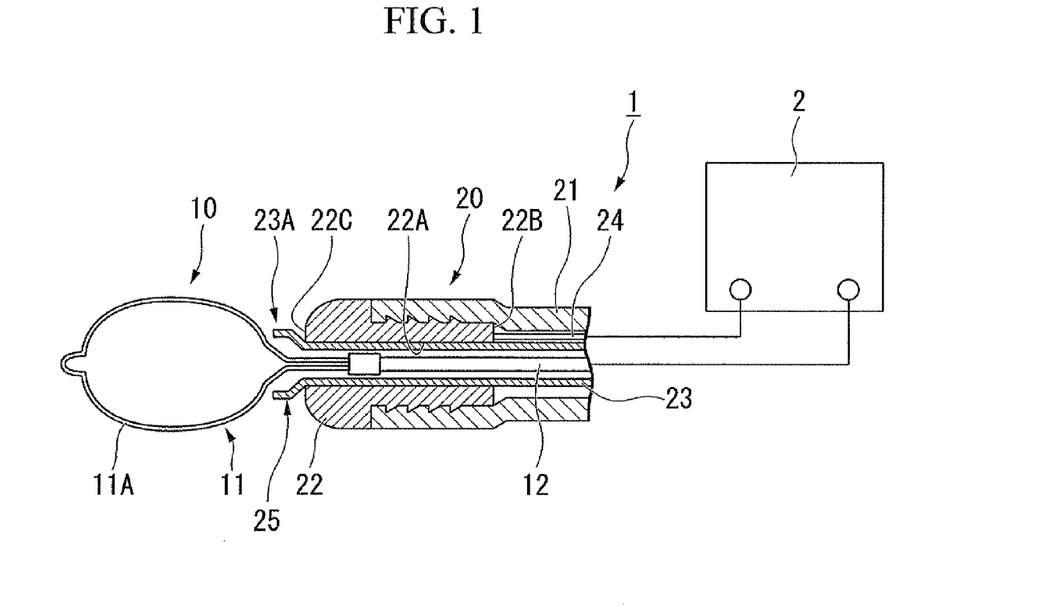
FIG. 1 A diagram of the configuration of a high-frequency treatment tool according to a first embodiment of the invention.

FIG. 1 is a diagram of the configuration of a high-frequency treatment tool 1 according to this embodiment. The high-frequency treatment tool 1 is a bipolar treatment tool used by inserting it into the forceps channel of an endoscope. The high-frequency treatment tool 1 includes a flexible elongated insertion part, a treatment part that is inserted into the insertion part such that it can be protruded from and receded into it, and an operation part that is connected to a proximal end of the insertion part and used in operating the treatment part.

FIG. 1 mainly illustrates the treatment part 10 and the distal-end part of the insertion part 20, and omits other parts of the insertion part 20, the operation part, and such like. The other parts of the insertion part 20, the operation part, and such like can be selected as appropriate from configurations of various types of publicly known treatment tools for endoscope including a high-frequency treatment tool.

As shown in FIG. 1, the treatment part 10 includes a snare wire 11 having a snare loop 11A. As described later, the snare wire 11 functions as a treatment electrode which a high-frequency current is passed through. A proximal end of the snare wire 11 is connected to a distal end of an operating wire 12. The operating wire 12 passes through the insertion part 20 and connects to the operation part. Therefore, by operating an operating mechanism such as a slider provided to the operation part, it is possible to advance and recede the treatment part 10 with respect to the insertion part 20 (to make it move relatively in the axial direction of the insertion part 20), and to make the treatment part 10 protrude from and recede into the insertion part 20.

The insertion part 20 includes an outer tube (second tube) 21 that forms an outermost layer, a passive electrode 22 attached to the distal end of the outer tube 21, and an inner tube (first tube) 23 inserted into the outer tube 21. The outer tube 21 is made from an insulating material such as resin, and is flexible. The passive electrode 22 is made from a conductive material, includes a through hole 22A extending in the axial direction, and is attached to the distal end of the outer tube 21 by pressing-in, adhesion, etc. A conducting wire 24 for supplying a high-frequency current to the passive electrode 22 is connected to a proximal-end part 22B of the passive electrode 22 positioned inside the outer tube 21.

Like the outer tube 21, the inner tube 23 is made from an insulating material such as resin, and is flexible. The inner tube 23 need not be made from the same material as the outer tube 21. The inner tube 23 is inserted into the through hole 22A in the outer tube 21 and the passive electrode 22, and the distal-end part 23A protrudes from the through hole 22A. With this configuration, the inner peripheral face of the through hole 22A in the passive electrode 22 is covered by the inner tube 23. Therefore, the operating wire 12 and the treatment part 10 inserted into the inner tube 23 are insulated from the passive electrode 22 and the conducting wire 24, preventing shorting between them.

A large-diameter part (engagement part) 25 has a diameter expanded by hot shaping, and is formed at the distal-end part 23A of the inner tube 23 protruding from the passive electrode 22. The outer diameter of the large-diameter part 25 is larger than the inner diameter of the through hole 22A in the passive electrode 22.

The operating wire 12 and the conducting wire 24 are each connected to a high-frequency power source 2. Thereby, a high-frequency current circuit containing the operating wire 12, the treatment part 10, the passive electrode 22, and the conducting wire 24 is formed on the high-frequency treatment tool 1.

An operation when using the high-frequency treatment tool 1 having the above configuration will be explained.

Firstly, an operator inserts an insertion part of an endoscope (not shown) into a body cavity of a patient, and advances the distal end of the insertion part to the vicinity of a tissue that is the object for treatment (object tissue), such as a polyp, while observing the inside of the body cavity.

The operator then inserts the insertion part 20 of the high-frequency treatment tool 1 into the forceps hole of the endoscope, and makes the distal end of the insertion part 20 protrude from the insertion part distal end of the endoscope. When performing this insertion, the operator preferably stores the treatment part 10 inside the insertion part 20 by operating the operation part of the high-frequency treatment tool 1. The high-frequency treatment tool 1 can also be inserted into the endoscope before the endoscope is inserted into the body cavity.

Figure 2:
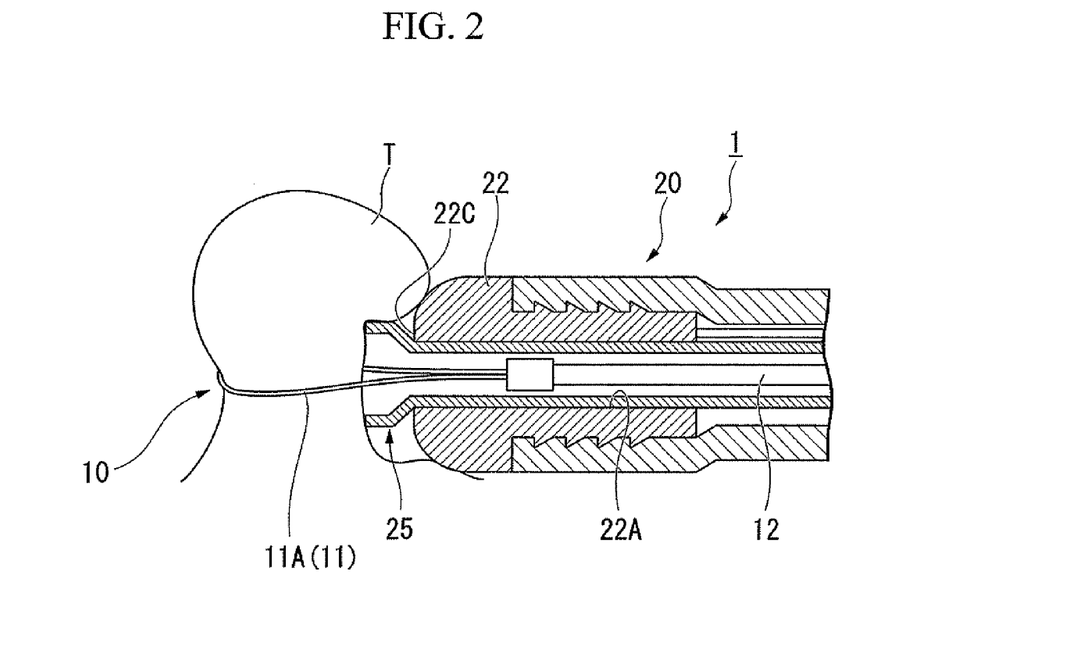
FIG. 2 A diagram of an operation when using the same high-frequency treatment tool.
Figure 3A:
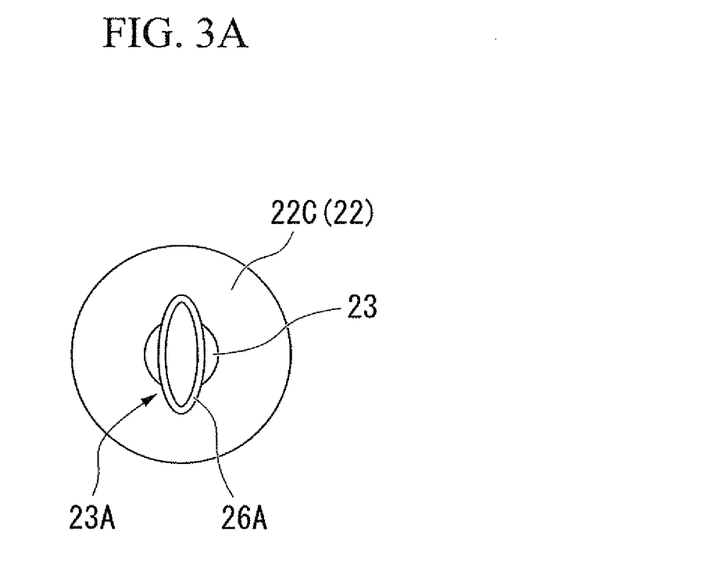
FIG. 3A A diagram of a modification of the same high-frequency treatment tool.
Figure 3B:
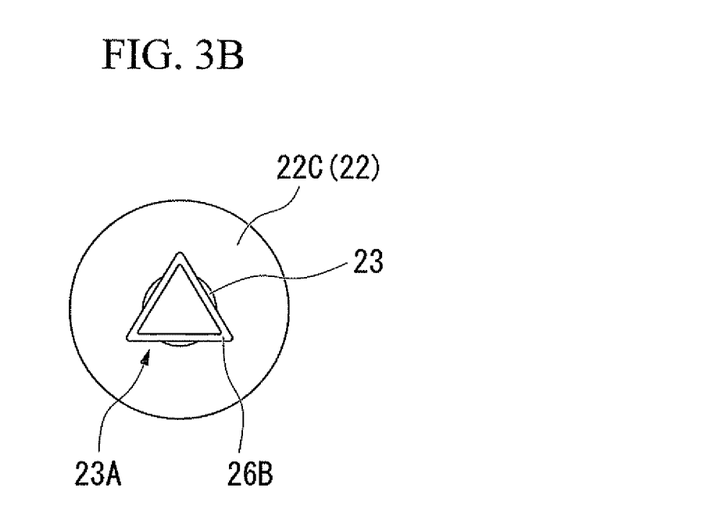
FIG. 3B A diagram of a modification of the same high-frequency treatment tool.

The operator then operates the operation part to make the treatment part 10 protrude from the distal end of the insertion part 20, and loops the snare loop 11A of the snare wire 11 around the object tissue. When the operator retracts the snare wire 11, as shown in FIG. 2, the object tissue T that is ensnared in the snare loop 11A contacts the passive electrode 22, and the snare wire 11 and the passive electrode 22 are electrically connected to each other with the object tissue T therebetween. If a high-frequency current from the high-frequency power source 2 is supplied in this state, the current passes through the object tissue T, which is thereby cauterized.

When the snare wire 11 is retracted, due to the object tissue T being drawn toward the distal end and the like, a force sometimes acts so as to retract the inner tube 23 with respect to the passive electrode 22 (so as to make it move relatively to the proximal-end side of the inner tube 23). However, the large-diameter part 25 provided at the distal end of the inner tube 23 engages with a distal-end face (engaged part) of the passive electrode 22. Therefore, the inner tube 23 is not pulled into the through hole 22A and its abovementioned relative movement is restricted. Since the inner face of the through hole 22A is consequently not covered by the inner tube 23 and is exposed, the inner tube 23 does not contact the treatment part 10 and the operating wire 12, and shorting is reliably prevented.

After the operator has cauterized the object tissue T, he removes the high-frequency treatment tool 1 from the endoscope. After the operator has, if necessary, performed another operation such as inserting another treatment tool, such as a gripping forceps, to collect the cauterized tissue, he removes the endoscope and ends this series of treatments.

According to the high-frequency treatment tool 1 of this embodiment, the large-diameter part 25 that can engage with the distal-end face 22C of the passive electrode 22 is formed on the inner tube 23, which ensures that the passive electrode 22 is insulated from the treatment part 10 and the operating wire 12 (hereinafter abbreviated as 'treatment part 10 etc.'). This favorably limits exposure of the inner peripheral face of the through hole 22A of the passive electrode 22 due to the distal-end part 23A of the inner tube 23 being pressed inside the outer tube 21. As a result, shorting between the passive electrode 22 and the treatment part 10 etc. is reliably prevented, and treatment can be performed favorably.

The large-diameter part 25 can easily be formed by executing hot shaping to deform the distal-end part 23A of the inner tube 23. This structure can thus easily be realized merely by executing a heating process to the distal-end part of the inner tube 23 inserted into the passive electrode 22, thereby achieving a high-frequency treatment tool that can be manufactured easily and efficiently.

Moreover, there is no need to use an adhesive agent or the like to fix the inner tube 23 to the inner wall of the through hole 22A. This simplifies the manufacturing step and eliminates the need for an adhesive agent and the like, enabling the high-frequency treatment tool 1 to be manufactured at lower cost.

In this embodiment, the example described is one where the engagement part is the large-diameter part 25 with a circular cross-section (including substantially circular), formed by hot shaping of the distal-end part 23A of the inner tube 23. However, since the relative movement of the inner tube 23 can be restricted if at least one part of the engagement part engages with the engaged part, the shape of the engagement part is not limited to the one described above. Therefore, as in the modifications shown in FIGS. 3A and 3B, one part of the outer peripheral face of the distal-end part 23A can be formed such that it protrudes radially outward to a sufficient extent that it can engage with the distal-end face 22C of the passive electrode 22. That is, the whole engagement part can be elliptical or oval like an engagement part 26A, or triangular like an engagement part 26B, or any other shape. To make FIGS. 3A and 3B easier to understand, they do not show the treatment part 10 and the operating wire 12 inserted into the inner tube 23.

Figure 4A:
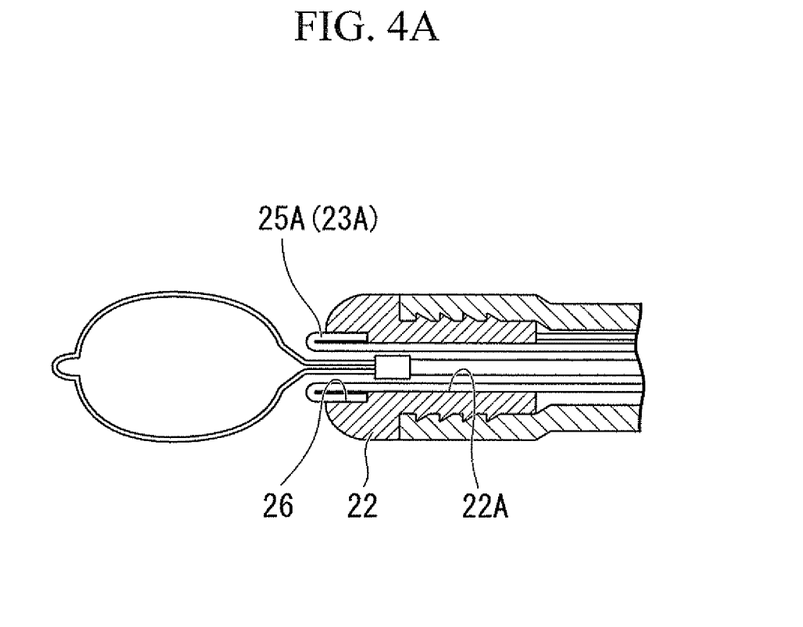
FIG. 4A A partial cross-sectional diagram of a distal-end part in a modification of the same high-frequency treatment tool.
Figure 4B:
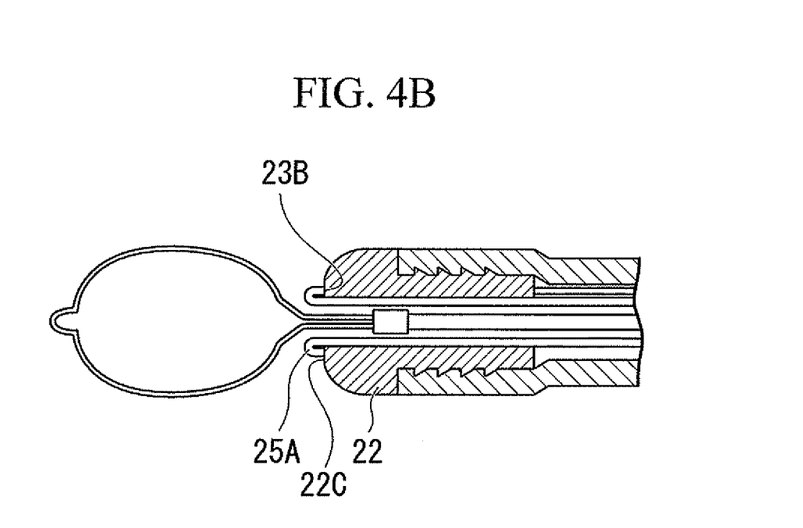
FIG. 4B A partial cross-sectional diagram of a distal-end part in a modification of the same high-frequency treatment tool.

As in the modifications shown in FIGS. 4A and 4B, the engagement part can be a large-diameter part 25A formed by executing hot shaping to fold the distal-end part 23A. In this case, as shown in FIG. 4A, the diameter of the distal-end side of the through hole 22A in the passive electrode 22 can be increased to form a storage part 26, and the large-diameter part 25A can be stored in this storage part 26. Alternatively, as shown in FIG. 4B, instead of working the passive electrode 22, the large-diameter part 25A can be protruded to the distal-end side of the passive electrode 22, and a distal-end face 23B of the folded inner tube 23 is made to engage with the distal-end face 22C of the passive electrode 22.

Subsequently, a second embodiment of the invention will be explained with reference to FIG. 5. A high-frequency treatment tool 31 of this embodiment differs from the high-frequency treatment tool 1 of the first embodiment in regard to the configuration of the engagement part. In the following explanation, configurative elements that are common to the embodiments already mentioned are designated with same reference numerals and are not repetitiously explained.

Figure 5:
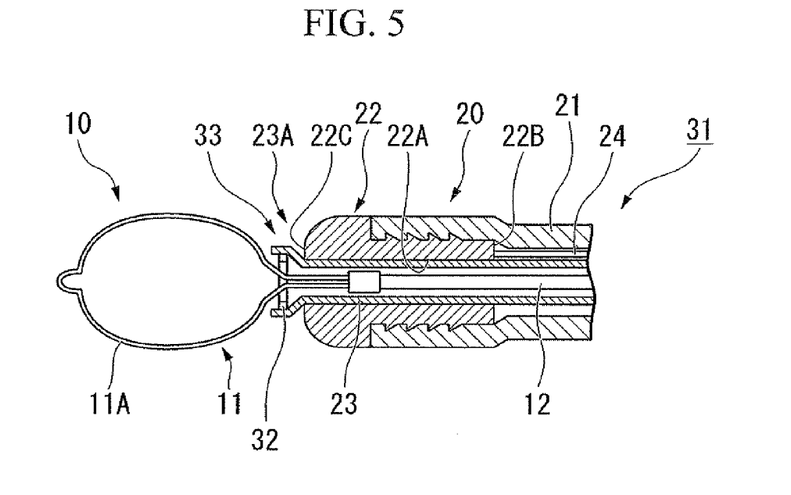
FIG. 5 A partial cross-sectional diagram of a distal-end part of a high-frequency treatment tool according to a second embodiment of the invention.

FIG. 5 is a partial cross-sectional diagram of a distal-end part of the high-frequency treatment tool 31. As shown in FIG. 5, a ring-shaped diameter-expanding member (shape-preserving member) 32 has an outer diameter larger than the inner diameter of the inner tube 23, and is pressed into the distal-end part 23A of the inner tube 23, thereby forming a large-diameter part 33.

While there are no particular restrictions on the material for the diameter-expanding member 32, it must be rigid enough to keep the large-diameter part 33 in a shape that can engage with the distal-end face 22C of the passive electrode 22. Specifically, an insulating material such as ceramics, or a metal material such as various types of stainless steel, can favorably be used.

Since shorting does not occur even if the diameter-expanding member 32 makes contact with the snare wire 11, it is not problematic to use a conductive material such as metal to form the diameter-expanding member. When the inner tube 23 is thin or the like, however, there is a possibility of shorting between the diameter-expanding member 32 and the passive electrode 22. Therefore, when using a conductive material to form the diameter-expanding member 32, the inner tube 23 is preferably made thick enough to sufficiently prevent shorting.

In the high-frequency treatment tool 31 of this embodiment, as in the high-frequency treatment tool 1 of the first embodiment, the inner peripheral face of the passive electrode 22 is reliably covered by the inner tube 23, whereby shorting can be favorably prevented.

Since the diameter-expanding member 32 having a predetermined rigidity is attached to the large-diameter part 33, the large-diameter part 33 can be formed simply and efficiently by pressing-in and the like, and its shape can be stably preserved. As a result, even if a large force attempts to retract the inner tube 23 with respect to the passive electrode 22, the relative movement of the inner tube 23 can be reliably restricted, ensuring insulation.

Subsequently, a third embodiment of the invention will be explained with reference to FIG. 6. A high-frequency treatment tool 41 of this embodiment differs from the high-frequency treatment tools of the embodiments described above in regard to the configuration of the insertion part.

Figure 6:
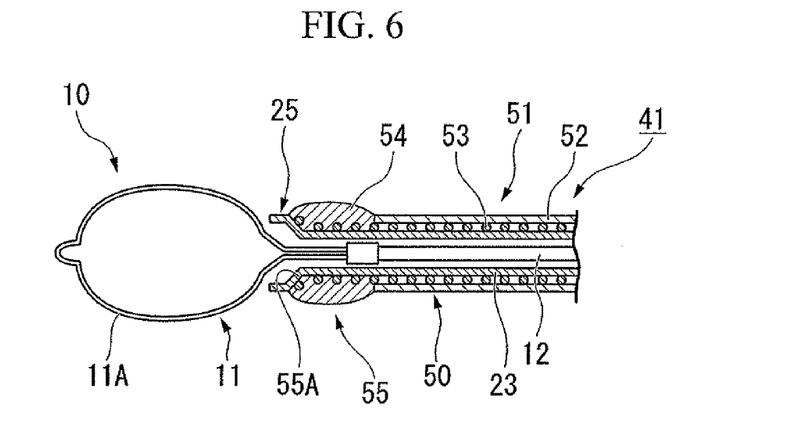
FIG. 6 A partial cross-sectional diagram of a distal-end part of a high-frequency treatment tool according to a third embodiment of the invention.

FIG. 6 is a cross-sectional diagram of the distal-end part of the high-frequency treatment tool 41. As shown in FIG. 6, the high-frequency treatment tool 41 includes an insertion part 50 instead of the insertion part 20. The insertion part 50 includes an outer tube 51 and an inner tube 23.

The outer tube 51 includes an outer-side tube main body 52 having insulating properties, and a tubular blade 53 disposed in an inner cavity of the tube main body 52. The blade 53 has a publicly known configuration woven from a plurality of metal wires. The inner tube 23 is inserted so as to cover the inner peripheral face of the tubular blade 53.

One part of the blade 53 protrudes from at the distal end of the tube main body 52, and is thus exposed. An electrode member 54 is electrically connected to the exposed blade 53, forming a passive electrode 55 at the distal end of the insertion part 50.

There are no particular restrictions on the method of disposing the electrode member 55. For example, the electrode member 55 can be fixed by applying brazing metal to the exposed blade 53, or a cylindrical conductive member can be fixed to the exposed blade 53 by brazing or the like.

The blade 53 extends to the proximal end of the insertion part 50, and one part of the metal wires constituting the blade 53 is connected to a high-frequency power source 2 (not shown). That is, the blade 53 functions as a conducting wire for connecting the passive electrode 55 to the high-frequency power source 2.

In the high-frequency treatment tool 41 of this embodiment, as in the high-frequency treatment tools of the embodiments described above, since the large-diameter part 25 engages with the distal-end face 55A of the passive electrode 55, the inner tube 23 reliably covers the inner peripheral face of the passive electrode 55, whereby shorting can be favorably prevented.

Since the current is passed through the blade 53 woven from metal wires, even if the insertion part 50 is subjected to a bending load or such like due to meandering in the body cavity or such like, the electrical connection between the passive electrode 55 and the high-frequency power source 2 is not easily broken, enabling the current to be passed reliably to the treatment part 10.

When manufacturing the insertion part 50 of this embodiment, a publicly known blade tube including a tubular blade layer and a covered layer made from resin and the like can favourably be used. In particular, if the blade tube includes a covered layer on the outer peripheral face and the inner peripheral face of the blade layer, the insertion part 50 can easily be formed. This insertion part 50 can easily be formed by exposing the blade layer by removing an outer-side covered layer having a predetermined length from the distal end, and then forming the passive electrode and expanding the diameter of the distal-end part by hot shaping or the like.

In this embodiment, the blade need not be tubular. Provided that it is connecting the high-frequency power source and the passive electrode, it can be disposed in one part of the inner peripheral face of the tube main body.

While preferred embodiments of the present invention have been described above, the invention is not limited to these embodiments. Additions, omissions, substitutions, and other modifications can be made to the configuration without departing from the scope of the invention.

Figure 7:
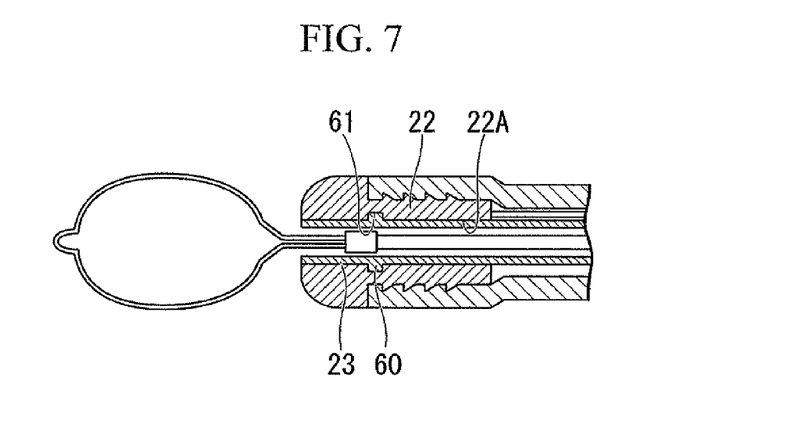
FIG. 7 A partial cross-sectional diagram of a distal-end part of a high-frequency treatment tool in a modification of the invention.
Figure 8:
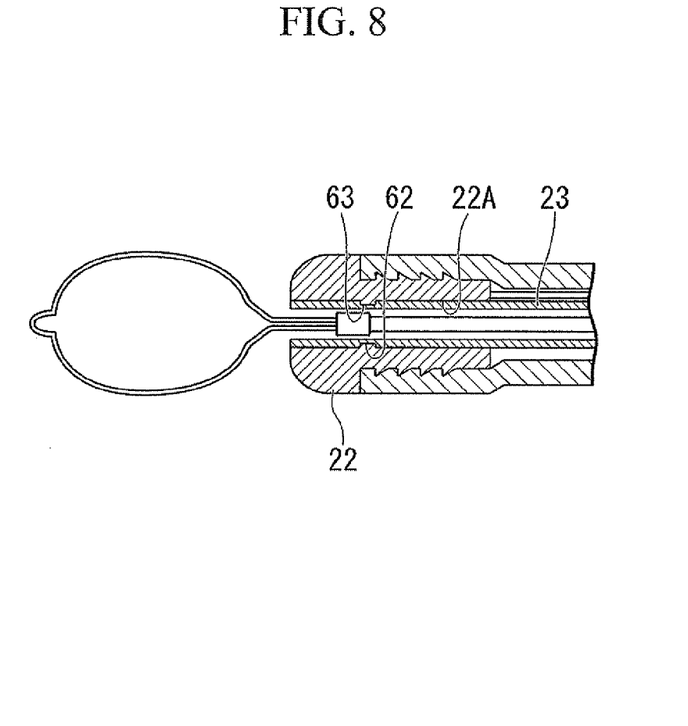
FIG. 8 A partial cross-sectional diagram of a distal-end part of a high-frequency treatment tool in a modification of the invention.

For example, though in each of the embodiments described above, the example described is one where the engagement part engages with the engaged part at the distal end of the insertion part, the engagement position is not limited to this one. As one example, in the modification shown in FIG. 7, it is possible to form a flange 60 as an engagement part on the proximal-end side at a predetermined length (e.g. approximately 10 mm) from the distal end of the inner tube 23, and to make this flange 60 engage with a groove 61 as an engaged part formed so as to extend in the circumferential direction on the inner peripheral face of the through hole 22A of the passive electrode 22. At this time, as in the modification shown in FIG. 8, the engagement part and the engaged part can be formed with an inverted protrusion/recess relationship by providing a groove 62 in the inner tube 23 and a protruding part 63 on the inner face of the through hole 22A. This makes it slightly more difficult to assemble the passive electrode 22 and the inner tube 23. Accordingly, it is preferable to assemble them by dividing the passive electrode 22 in the axial direction and disposing the inner tube 23 such that it is sandwiched by the divided members, thereby facilitating assembly.

Figure 9:
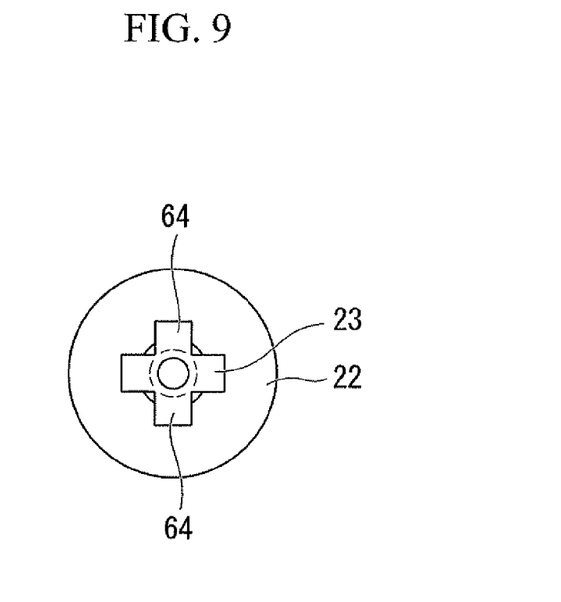
FIG. 9 A diagram of a high-frequency treatment tool in a modification of the invention.

As in the modification shown in FIG. 9, an engagement part 64 can be formed by forming a notch extending in the axial direction in the distal end of the inner tube 23, and executing hot shaping or the like to fix a state where the outer peripheral face of the distal-end part 23A, which is divided into a plurality, is folded radially outward at this notch.

Figure 10A:
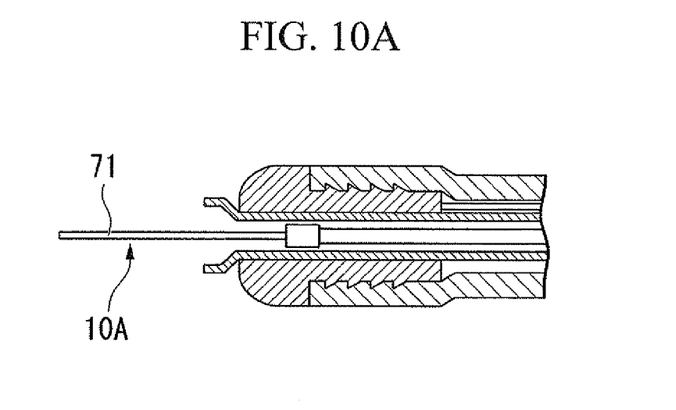
FIG. 10A A partial cross-sectional diagram of a distal-end part of a high-frequency treatment tool in a modification of the invention.
Figure 10B:
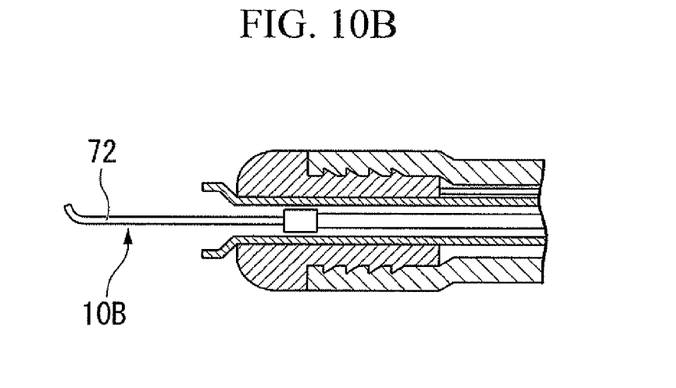
FIG. 10B A partial cross-sectional diagram of a distal-end part of a high-frequency treatment tool in a modification of the invention.
Figure 10C:
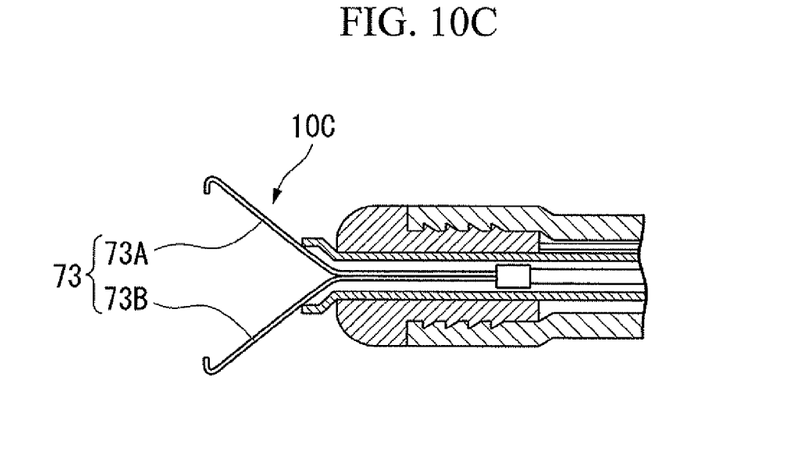
FIG. 10C A partial cross-sectional diagram of a distal-end part of a high-frequency treatment tool in a modification of the invention.

Moreover, while in the examples described in each of the embodiments, the treatment part includes a snare wire having a snare loop that functions as a treatment electrode, the shape of the treatment part is not limited to this one. That is, various treatment part shapes can be applied to a bipolar high-frequency treatment tool. For example, as shown in FIG. 10A, a treatment part 10A can include a needle knife 71 as a treatment electrode. Furthermore, as shown in FIG. 10B, a treatment part 10B can include a hook knife 72 as a treatment electrode. Moreover, as shown in FIG. 10C, a treatment part 10C can include a two-legged forceps 73, including a pair of gripping parts 73A and 73B arranged such that their distal ends are set apart, as a treatment electrode.

Figure 11:
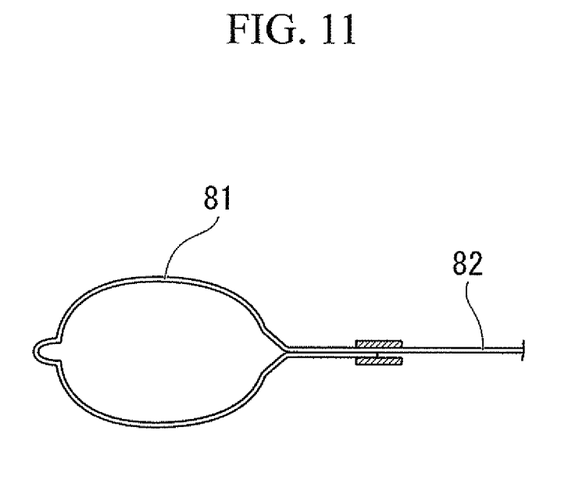
FIG. 11 A diagram of high-frequency treatment tool and an operating wire in a modification of the invention.

Though in the examples described in each of the embodiments, the treatment part and the operating wire are formed as separate members and then connected, as shown in FIG. 11, a snare wire 81 and an operating wire 82 can be formed as a single wire. Similarly, when the high-frequency treatment tool of the invention includes another treatment part, including the various types of treatment parts shown in FIGS. 10A to 10C, at least one part of this treatment part can be formed as a single wire with the operating wire.

The configurations of the each of the embodiments and modifications described above can be combined as appropriate.

INDUSTRIAL APPLICABILITY

The high-frequency treatment tool according to the invention can be manufactured easily and efficiently, and can prevent shorting between the treatment electrode and the passive electrode.

REFERENCE NUMERALS 1, 31, 41 HIGH-FREQUENCY TREATMENT TOOL 1
10, 10A, 10B, 10C TREATMENT PART (TREATMENT ELECTRODE)
11, 81 SNARE WIRE (TREATMENT ELECTRODE)
12, 82 OPERATING WIRE
21, 51 OUTER TUBE (SECOND TUBE)
22, 55 PASSIVE ELECTRODE
22C, 55A DISTAL-END FACE (ENGAGED PART)
23 INNER TUBE (FIRST TUBE)
25, 25A, 33 LARGE-DIAMETER PART (ENGAGEMENT PART)
26A, 26B ENGAGEMENT PART
32 DIAMETER-EXPANDING MEMBER (SHAPE-PRESERVING MEMBER)
52 Tube Main Body
53 BLADE
71 NEEDLE KNIFE (TREATMENT ELECTRODE)
72 HOOK KNIFE (TREATMENT ELECTRODE)
73 TWO-LEGGED FORCEPS (TREATMENT ELECTRODE)
73A, 73B GRIPPING PARTS

The invention claimed is:
1. A high-frequency treatment tool comprising:
an operating wire having a treatment part including a treatment electrode;
a first tube formed from an insulating material, in which the operating wire for enabling the treatment part to protrude and recede is inserted; and
a second tube having a passive electrode with a distal-end face at a distal end, in which the first tube is inserted so as to cover an inner peripheral face of the passive electrode;
wherein a large-diameter part formed in a distal-end part of the first tube contacts the distal-end face of the passive electrode;
the passive electrode includes a through-hole extending in the axial direction of the passive electrode;
an outer diameter of the large-diameter part is larger than an inner diameter of the through-hole; and a retraction of the distal-end part of the first tube into the through-hole is restricted by an engagement of the large-diameter part and the distal-end face of the second tube.

2. The high-frequency treatment tool according to claim 1, wherein the large-diameter part is formed by hot shaping at the distal-end part of the first tube.

3. The high-frequency treatment tool according to claim 1, wherein the large-diameter part is formed by pressing-in a shape-preserving member at the distal-end part of the first tube.

4. The high-frequency treatment tool according to claim 1, wherein the second tube includes a flexible tube main body, and a blade comprising metal wires that is inserted into an inner cavity of the tube main body; and the blade and the passive electrode are electrically connected.

5. The high-frequency treatment tool according to claim 1, wherein an outer diameter of other parts of the first tube excluding the large-diameter part is substantially the same as the inner diameter of the through-hole.

* * * * *